US00PP19539P3

(12) United States Plant Patent
van den Top

(10) Patent No.: US PP19,539 P3
(45) Date of Patent: Dec. 2, 2008

(54) *HOSTA* PLANT NAMED 'LITTLE JAY'

(50) Latin Name: *Hosta*
Varietal Denomination: Little Jay

(76) Inventor: Hendrik Jan van den Top, Wesselseweg 46, Barneveld (NL), 377 1PC ( * ) Notice: Subject to any disclaimer, the term of this patent is extended or adjusted under 35 U.S.C. 154(b) by 0 days.

(21) Appl. No.: 11/704,810

(22) Filed: Feb. 9, 2007

(65) Prior Publication Data

US 2008/0196134 P1 Aug. 14, 2008

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent L. Bell
*Assistant Examiner*—June Hwu

(57) ABSTRACT

A new and distinct *Hosta* plant named 'Little Jay' characterized by lance-leafed, dwarfsized, leaves with blue green margins, light yellow to creamy leaf centers, vertical flower scapes with light purple flowers, suitable for landscape, potted culture, or cut flower arrangements.

2 Draing Sheets

Botanical classification: *Hosta* hybrid (Tratt.).
Variety denomination: 'Little Jay'.

SUMMARY, BACKGROUND AND ORIGIN OF THE PLANT

The present invention relates to the new and distinct *hosta* plant, *Hosta* 'Little Jay' discovered by Hendrik Jan van den Top at a nursery in The Netherlands. The Plant is an uninduced whole plant sport of the *Hosta* cultivar 'Beauty Little Blue' (not patented). 'Beauty Little Blue' is a cross of *Hosta* 'Blue Cadet' (not patented) with *Hosta clausa* var. *normalis* (not patented). The plant has been successfully asexually propagated by division and tissue culture methods at a plant nursery in Barneveld, The Netherlands and found to produce identical plants that maintain the unique characteristics of the original plant. The plant is stable and reproduces true to type in successive generations of asexual reproduction.

*Hosta* 'Little Jay' differs from its parents, as well as all other *hostas* known to the applicant, in that the plant has a very narrow variegated leaf that emerges with the center pale yellow in the spring and with sunlight and warmer temperatures lightens to a white. The leaf margin is green with a slight glaucous bloom producing a slightly bluish cast.

The most similar known *hosta* cultivar is *Hosta* 'Fireworks' U.S. Plant Pat. Ser. No. 16,062. 'Fireworks' has a larger and wider leaf, does not start up as yellow in the center, and the flower is lighter lavender.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
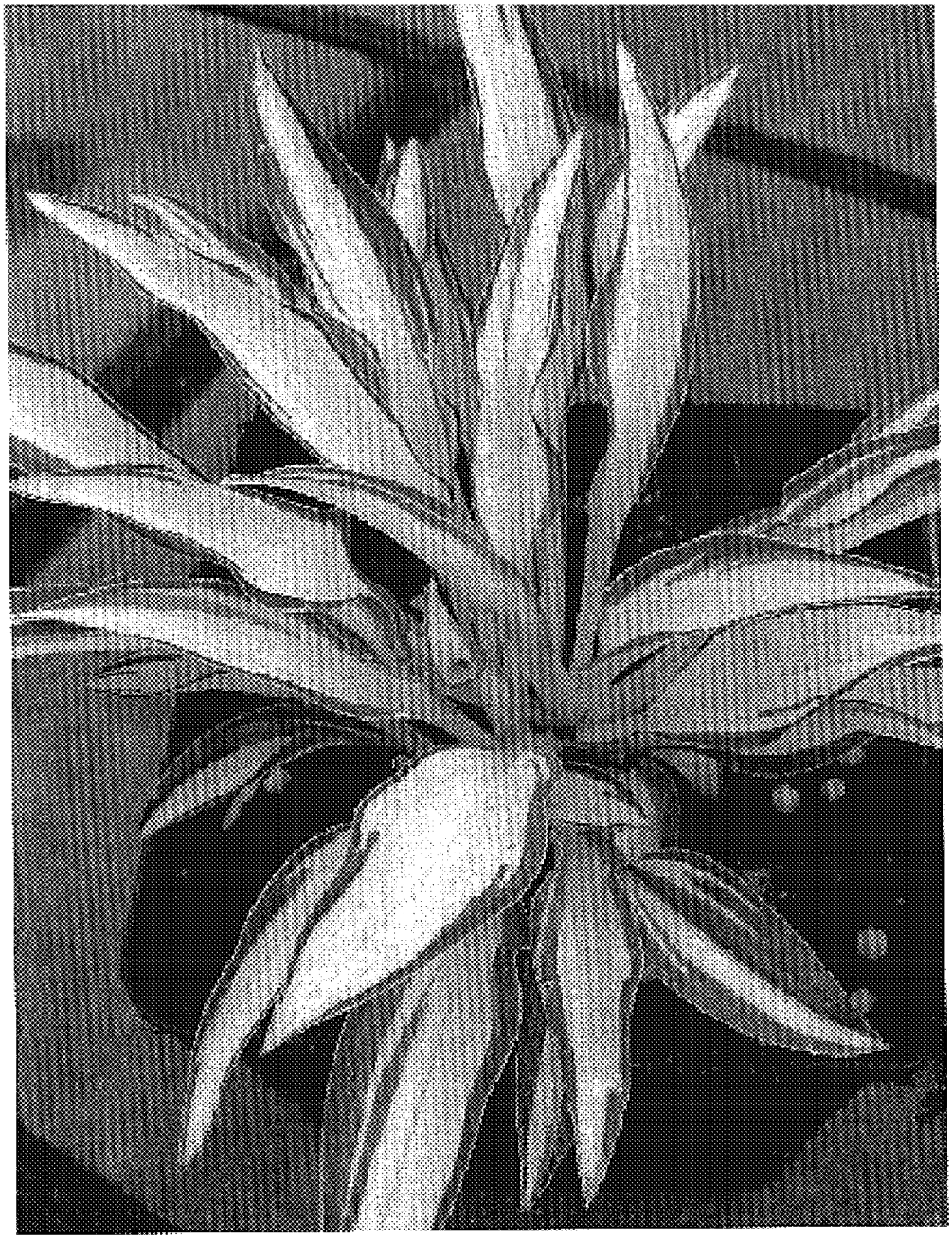
FIG. 1 shows the foliage early in the season in Barneveld, Netherlands.
Figure 2:
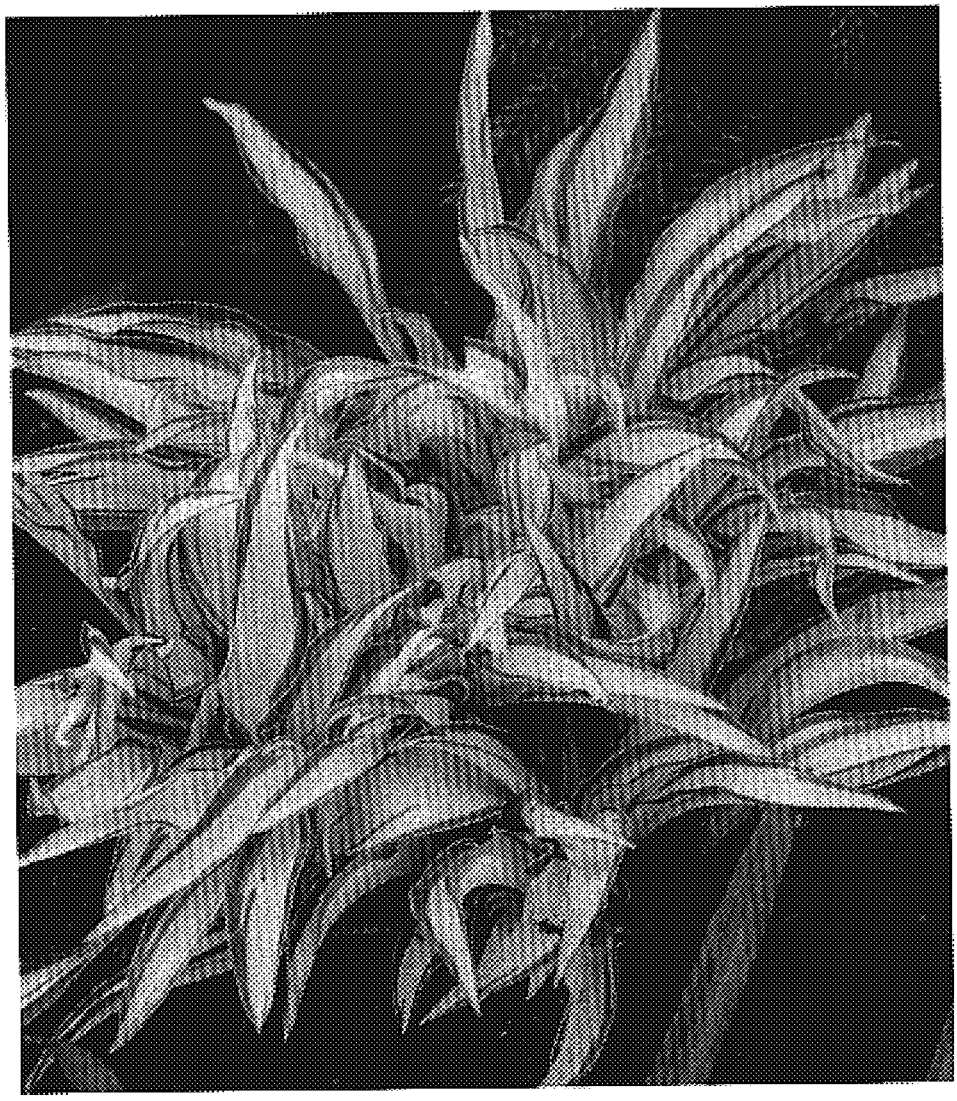
FIG. 2 shows the foliage after flowering in Barneveld, Netherlands.

There are about 3,500 cultivars registered with The American *Hosta* Society, which is the International Cultivar Registration Authority for the genus *Hosta*. *Hosta* 'Little Jay' differs from these and all unregistered cultivars known to the inventor in that it has:

1. Long lance-like blue green foliage with a light yellow becoming creamy white center portion of the leaf;
2. Short habit, small-sized clumps with medium purple flowers on creamy yellow scapes.

DETAILED BOTANICAL DESCRIPTION

The following descriptions and color references are based on the 2001 edition of The Royal Horticultural Society Colour Chart except where common dictionary terms are used. The new plant, *Hosta* 'Little Jay', has not been observed under all possible environments. The phenotype may vary slightly with different environmental conditions, such as temperature, light, fertility, moisture and maturity levels, but without any change in the genotype. The following observations and size descriptions are of a two-year old containerized plant in a nursery in Barneveld, Netherlands under controlled shade canopy with supplemental water and fertilizer.

Botanical classification: *Hosta* hybrid.
Parentage: naturally occurring sport of *Hosta* 'Beauty Little Blue' (not patented).
Propagation:
*Method.*—By sterile laboratory tissue culture division and garden division; Time to initiate roots from tissue culture: about four weeks; Rooting habit: normal, fleshy, lightly branching.
Plant description:
*Plant shape and habit.*—Hardy herbaceous perennial with basal rosette leaves, symmetrical and arching over, spreading by rhizomes.
*Crop time.*—Under normal summer growing conditions 18 to 20 weeks to finish in a one-liter container; plant vigor is good to high in comparison to other center variegated *hostas*.

*Plant size.*—Foliage height at flowering is 11 to 15 cm tall from soil line to the top of the leaves and 20 to 25 cm wide above the soil line.

Foliage description:

*Shape and size.*—Elliptic to lanceolate leaf blades, narrowly acute apex and base acutely tapered toward petiole. The leaf blades are 6 to 9 cm long and 2.5 to 3.0 cm wide; margin is entire, and the variegation pattern on the darker edge varies in different regions of the leaf from 2 to 8 mm wide; 4 and 6 pairs of major parallel veins the same color as the surrounding leaf tissue on the top and bottom of the leaves; top and bottom surfaces are dull without slight glaucous bloom; Color of young emerging leaves: Top center surface: between RHS 3B and RHS 3C; Top margin surface: between RHS 141B and RHS 143A; Underside center: RHS 3D; Underside margin: RHS 141B with some intermediate between the margin and center on both top and bottom of RHS N144A and lighter than RHS N144C. Color of mature leaves: Top surface center: lighter than RHS 2D; top surface margin: RHS 133A with some intermediate colors of RHS 133 C and RHS 144C; Underside center: closest to RHS 2D; underside margin: closest to RHS 133B with intermediate colors of RHS 133 D and lighter than RHS 133D.

*Petioles.*—3 to 5 cm long and about 5 mm wide. The leaf margin variegation continues down the petiole about 1 mm wide of RHS 141 C on young foliage on both top and underside, and center is nearest RHS 154 D on both surfaces. On older foliage the petiole the margin of both surfaces is RHS 143 B, and both surfaces of the center are lighter than RHS 2D.

Flower description:

*Buds.*—One day prior to opening about RHS 85 C; approximately 3.2 cm long, up to 1.0 cm wide, clavate with acute ovoid apex and longer thin base.

*Flowers.*—10 to 18 per scape; funnelform; 2.5 to 2.8 cm wide and about 3.5 cm long, (distal flowers being smaller), persists for a normal period, usually one day on or cut from plant, and the scapes remain effective from mid July into August. No detectable fragrance.

*Tepal.*—Two sets of three fused at the base; clavate with acute apex; entire; approximately 3.5 cm long and 1.0 cm wide, about RHS N82 D on the outside of both sets becoming lighter toward the base; inside about RHS N 76 C.

*Gynoecium.*—Single; Style—3.5 to 3.8 cm long, white, lighter than RHS 11 D, 1 mm diameter, slightly curved at distal end; Stigma—1 mm to 2 mm in diameter, white, lighter than RHS 11 D; Androecium—Filaments—six, white, lighter than RHS 11 D, less than 1 mm in diameter, about 3.0 cm long; Anthers—4 mm long, 1.0 mm wide, RHS 83B; Pollen—elliptical, less than 0.1 mm long, nearest RHS 15 A;

*Bracts.*—Bracts below flowers sessile, completely or nearly completely wrapped around scape; normally up to 1.5 cm long and 8 mm wide; smaller and protruding when subtending flowers; margin of both surfaces RHS 141 B; center of both surfaces when exposed to direct sun between RHS 3C and RHS 3D;

*Peduncle.*—One per mature division, approximately six per clump; erect 20 to 28 cm tall and about 4 mm in diameter, pale yellow color RHS 3D with slight glaucous surface.

*Pedicel.*—Approximately 0.6 cm long and 2 mm wide; RHS 3C; curled slightly downward.

*Fruit.*—Viable seed has not been observed.

Disease resistance: Resistance beyond that of other *hostas* has not been observed. The plant grows best with plenty of moisture and adequate drainage, but is able to tolerate some drought when mature. Hardiness at least from USDA zone 3 through 9, and other disease resistance is typical of that of other *hostas*.

I claim:

1. A new and distinct cultivar of ornamental *Hosta* plant named 'Little Jay' herein described and illustrated, with lance-like leaves of light yellow to cream in the center and blue green margins, with light purple flowers and dwarf habit, suitable as a potted plant, for the garden, and for cut flower arrangements.

* * * * *